United States Patent [19]

Smith

[11] 3,960,971

[45] June 1, 1976

[54] PROCESS FOR PREPARING ALLYLIC ALCOHOLS

[75] Inventor: William E. Smith, Schenectady, N.Y.

[73] Assignee: General Electric Company, Pittsfield, Mass.

[22] Filed: Mar. 13, 1974

[21] Appl. No.: 450,586

[52] U.S. Cl. .............................. 260/638 R; 252/471; 252/475; 260/491; 423/155; 423/164
[51] Int. Cl.² ....................................... C07C 29/00
[58] Field of Search ..................... 260/638 R, 491

[56] References Cited
UNITED STATES PATENTS

| | | | |
|---|---|---|---|
| 1,433,308 | 10/1972 | Steffens | 260/491 |
| 2,388,164 | 10/1945 | Loder | 260/491 |
| 2,578,647 | 12/1951 | Stiteler et al. | 260/491 |
| 2,666,771 | 1/1954 | Zettlemoyer et al. | 260/638 R |
| 3,328,439 | 6/1967 | Hamilton | 260/638 R |
| 3,748,282 | 7/1973 | Evans | 423/155 |

OTHER PUBLICATIONS

Torraco and Torriziani, "Chim, Ind.," (Milan), 44, 483–488, (1962).

*Primary Examiner*—Joseph E. Evans
*Attorney, Agent, or Firm*—Donald M. Papuga; William F. Mufatti

[57] ABSTRACT

A vapor phase process for preparing allylic alcohols which comprises reacting an allylic ester of a lower alkyl carboxylic acid with a lower alkanol in the presence of a transesterification catalyst comprising magnesia.

4 Claims, No Drawings

PROCESS FOR PREPARING ALLYLIC ALCOHOLS

This invention relates to a process for preparing allylic alcohols which comprises reacting an allylic ester of a lower carboxylic acid with a lower alkanol, in the vapor phase and in the presence of a magnesia transesterification catalyst.

BACKGROUND OF THE INVENTION

Allyl alcohol has been prepared by a number of different methods. Most prominent among them are the rearrangement of propylene oxide (French Patent 1,496,221) and the hydrolysis of allyl chloride (Japanese Patent 70 10,126) and allyl acetate (Japanese Patent 73 10,767). The latter two methods particularly are suitable for preparation of a variety of allylic alcohols.

The homogenous liquid phase methanolysis of allyl acetate under the influence of metal alkoxide and hydroxide catalysts has been described (German Patent 1,939,142). With this method, however, the catalyst is gradually consumed in side reactions and is not conveniently recycled.

The liquid phase transesterification of dimethyl terephthalate and ethylene glycol promoted by magnesia (Torraco and Turriziani, *Chim, Ind.* (Milan), 44, 483–8 (1962)) has also been described.

DESCRIPTION OF THE INVENTION

It has been discovered that allylic alcohols may be produced with high efficiency by reaction of the corresponding carboxylate esters with lower alkanols in the vapor phase and in the presence of a magnesia transesterification catalyst. In addition to the advantages inherent in a stationary, heterogenous catalyst, the magnesia in this process is selective with respect to the transesterification reaction, and is not subject to destruction in side reactions.

The process is illustrated, for the case of preparation of allyl alcohol by methanolysis of allyl acetate, in Equation (1).

magnesium oxide, magnesium hydroxide, mixtures of these two, and their mixtures containing inert substances such as magnesium silicate. Magnesia compositions of the type described in U.S. Pat. No. 3,748,282 are particularly active in promoting the transesterification process. These catalysts are composed of magnesium oxide, magnesium hydroxide and a manganese oxide promoter. This patent is incorporated herein by reference.

The temperatures at which the process can be carried out vary widely. Temperatures ranging from about 100°C. to 250°C. are generally adequate. Preferably the reaction is carried out at temperatures of from about 150° C. to about 225°C. The maximum depends upon destruction of the reactants or products, dehydration and dehydroacyloxylation reactions occuring under too vigorous conditions.

Although only atmospheric pressure is normally required, it will be of course apparent to those skilled in the art that superatmospheric or subatmospheric pressure may be used where conditions so dictate.

In carrying out the process, a vapor phase mixture of the allylic ester and alkanol (the latter usually in substantial excess) is passed through a heated bed of the catalyst. The effluent is distilled directly, affording the allylic alcohol and alkyl ester products, in addition to the alkanol and unconverted allylic ester, which are recycled to the reaction zone. In the case of preparing allyl alcohol by methanolysis of allyl acetate particularly, the methyl acetate-methanol azeotrope, methanol, allyl alcohol and allyl acetate are easily separated by simple distillation, a situation much more favorable than when water is present in hydrolysis processes.

As described in copending applications of William E. Smith and R. John Gerhart, Ser. Nos. 439,275, 439,276, and 439,277, all filed Feb. 4, 1974 and all assigned to the same assignee as this invention, carboxylic acid esters can be employed as feedstock in processes for preparing allylic esters by oxidation of the appropriate olefins. Thus, with recycle of the alkyl carboxylate co-product an efficient and economical overall process for producing allylic alcohols from ole-

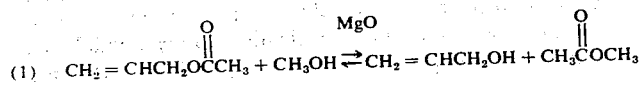

The process may be employed for the production of a wide variety of allylic alcohols. Allyl alcohol, methallyl alcohol and crotyl alcohol in particular are efficiently produced in this way, derived from the corresponding allyl, methallyl and crotyl carboxylate esters. The carboxylate moieties in these esters are those derived from the lower alkyl carboxylic acids, i.e., those having from one to six carbon atoms. A preferred class of carboxylate esters is the acetates. The lower alkanol may be selected from those having from one to six carbon atoms, with methanol a preferred alkanol.

The catalysts that may be employed in this invention are magnesia in its various forms generally, including fins is possible, as illustrated in Equations (2) and (3) for the case of preparing allyl alcohol from propylene.

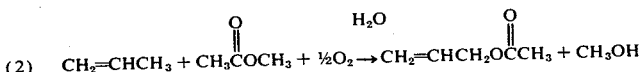

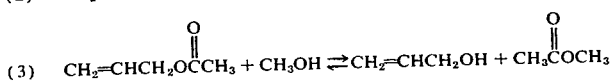

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE 1

Apparatus

A vertical hot tube reactor (16mm ID × 70cm effective length) was constructed from heavy wall glass, with 24/40 male and female joints. Vigreaux points were indented just above the male joint to support catalyst pellets. Thermocouple leads were fastened into three other Vigreaux indentations at points along the length. Three 4 ft. × 1 in. Briskheat glass insulated heating tapes were wound onto the tube, covered with glass wool and glass tape, and connected to separate variable transformers. The tube exit was connected by a gooseneck (also heated) to an efficient condenser and collection vessel. A three-neck flask served as the evaporator, with the reactants added from an addition funnel in a side neck. A nitrogen carrier gas was passed through to provide contact times on the order of 3 to 10 seconds.

The tube described above was charged with 152 g. of magnesia catalyst (Harshaw Mg 0601 T, ⅛ in. extruded pellets). After pretreatment with methanol vapor at 200°–220°C. the tube was maintained at that temperature range while a mixture of 50 g. of allyl acetate and 150 g. of methanol was passed through over 1.5 hours. Quantitative glpc analysis of the effluent showed the presence of 9.1 g. of unconverted allyl acetate (18% recovery), 21.7 g of allyl alcohol (91% yield based on 82% conversion), 27.9 g of methyl acetate (92% yield) and the excess methanol. The allyl alcohol could be readily isolated by distillation.

EXAMPLE 2

The tube described in Example I was charged with 79.1 grams of "magnesia" catalyst (3/16 in. pills, manufactured by Dart Industries) containing about 45% magnesium hydroxide and 4% manganese oxide in addition to the magnesium oxide (50%), and operated with the same conditions and procedure as in Example I. Analysis of the effluent in this case showed the presence of 3.8 g of unconverted allyl acetate (8% recovery), 24.9 g of allyl alcohol (90% yield based on 92% conversion), 30.7 g of methyl acetate (90% yield) and the excess methanol.

EXAMPLE 3

The tube, catalyst and general procedure described in Example 2 were employed, with the operating temperature reduced to 130°–150°C. The effluent in this case was composed of 9.4 g of unconverted allyl acetate (19% recovery), 22.6 g of allyl alcohol (96% yield based on 81% conversion), 27.9 g of methyl acetate (93% yield) and the excess methanol.

EXAMPLE 4

The tube, catalyst and general procedure described in Example 2 were employed, with 57.0 g of methallyl acetate substituted for the allyl acetate. The effluent in this case was composed of 12.5 g of unconverted methallyl acetate (22% recovery), 27.8 g of methallyl alcohol (99% yield based on 78% conversion), 26.8 g of methyl acetate (93% yield) and the excess methanol.

EXAMPLE 5

The tube, catalyst and general procedure described in Example I were employed, with 57.0 g of crotyl acetate substituted for the allyl acetate. The effluent in this case was composed of 12.5 g of unconverted crotyl acetate (22% recovery), 24.7 g of crotyl alcohol (88% yield based on 78% conversion), 24.5 g of methyl acetate (85% yield) and the excess methanol.

It should, of course, be apparent to those skilled in the art that changes may be made in the particular embodiments of the invention described which are within the full intended scope of the invention as defined by the appended claims.

What is claimed is:

1. A vapor phase process for preparing an allylic alcohol which comprises reacting an allylic ester of a lower carboxylic acid selected from the group consisting of allyl acetate, methallyl acetate or crotyl acetate with a lower alkanol in the presence of a transesterification catalyst which is a mixture of magnesium oxide, magnesium hydroxide and manganese oxide at a temperature of from about 100°C to about 250°C.

2. The process of claim 1 wherein the allylic ester is allyl acetate.

3. The process of claim 1 wherein the lower alkanol is methanol.

4. A vapor phase process for preparing allyl alcohol which comprises reacting allyl acetate with methanol in the presence of a transesterification catalyst which is a mixture of magnesium oxide, magnesium hydroxide and manganese oxide at a temperature of from about 100°C to about 250°C.

* * * * *